(12) United States Patent
Guymon

(10) Patent No.: US 9,654,742 B2
(45) Date of Patent: May 16, 2017

(54) SYSTEM AND METHOD OF AUTOMATICALLY DETERMINING MATERIAL REACTION OR SENSITIVITY USING IMAGES

(71) Applicant: Safety Management Services, Inc., West Jordan, UT (US)

(72) Inventor: Clint Guymon, South Jordan, UT (US)

(73) Assignee: Safety Management Services, Inc., West Jordan, UT (US)

( * ) Notice: Subject to any disclaimer, the term of this patent is extended or adjusted under 35 U.S.C. 154(b) by 0 days.

(21) Appl. No.: 14/954,986

(22) Filed: Nov. 30, 2015

(65) Prior Publication Data

US 2016/0112682 A1    Apr. 21, 2016

Related U.S. Application Data

(63) Continuation-in-part of application No. 13/691,450, filed on Nov. 30, 2012, now Pat. No. 9,202,145.

(51) Int. Cl.

| | | |
|---|---|---|
| *G06K 9/00* | (2006.01) | |
| *H04N 7/18* | (2006.01) | |
| *H04N 5/235* | (2006.01) | |
| *G06K 9/78* | (2006.01) | |
| *G06K 9/62* | (2006.01) | |
| *G06T 7/00* | (2017.01) | |
| *G01N 21/88* | (2006.01) | |

(52) U.S. Cl.
CPC ............ *H04N 7/183* (2013.01); *G01N 21/88* (2013.01); *G06K 9/6277* (2013.01); *G06K 9/78* (2013.01); *G06T 7/001* (2013.01); *H04N 5/2351* (2013.01); *G06T 2207/30108* (2013.01)

(58) Field of Classification Search
CPC .................................................. G06K 2209/09
See application file for complete search history.

(56) References Cited

U.S. PATENT DOCUMENTS

| | | | | |
|---|---|---|---|---|
| 5,993,194 A | * | 11/1999 | Lemelson | ............... F23N 5/082 356/418 |
| 6,134,342 A | * | 10/2000 | Doke | ................. G01M 11/0278 356/124 |
| 6,282,462 B1 | * | 8/2001 | Hopkins | ............... G06T 1/0007 348/314 |

(Continued)

OTHER PUBLICATIONS

Reeves et al ("Thermal and Impact Reaction Initiation in Ni/Al Heterogeneous Reactive Systems", 2010).*

(Continued)

*Primary Examiner* — Avinash Yentrapati
(74) *Attorney, Agent, or Firm* — Terrence J. Edwards; TechLaw Ventures, PLLC

(57) ABSTRACT

The disclosure extends to systems, methods and computer program products for automatically determining whether an energetic substance or a material has experienced a reaction ("go") or a non-reaction ("no-go") during an insult from an impact, friction, ESD or other small-scale sensitivity testing device. The systems, methods, and computer program products of the disclosure use a video capturing device, a CPU or computer, sensitivity test equipment, and a set of rules or instructions to be followed for quantifying and determining whether a reaction has occurred or not.

48 Claims, 17 Drawing Sheets

(56) References Cited

U.S. PATENT DOCUMENTS

| | | | | |
|---|---|---|---|---|
| 6,535,623 | B1* | 3/2003 | Tannenbaum | G06T 7/0083 382/128 |
| 6,545,715 | B1* | 4/2003 | Na | H04N 5/23212 348/252 |
| 6,643,412 | B1* | 11/2003 | Hong | G06F 17/153 382/279 |
| 6,937,743 | B2* | 8/2005 | Rizzotti | G08B 17/125 340/578 |
| 7,098,945 | B1* | 8/2006 | Sasai | H04N 9/735 348/223.1 |
| 7,177,474 | B2* | 2/2007 | Hougui | H04N 7/122 345/589 |
| 7,505,604 | B2* | 3/2009 | Zakrzewski | B64D 45/0015 382/100 |
| 7,693,326 | B1* | 4/2010 | Luo | H04N 19/132 382/162 |
| 7,983,458 | B2* | 7/2011 | Wang | A61B 1/00009 348/699 |
| 8,088,332 | B2* | 1/2012 | Haas | G01N 21/8483 422/400 |
| 8,094,929 | B2* | 1/2012 | Ogasawara | G01N 21/783 356/402 |
| 8,164,594 | B2* | 4/2012 | Watanabe | G06T 15/506 345/426 |
| 8,208,723 | B2* | 6/2012 | Yamagishi | G08B 17/125 382/100 |
| 8,231,748 | B1* | 7/2012 | Higa | C06B 21/0066 149/108.2 |
| 8,311,345 | B2 | 11/2012 | Chu et al. | |
| 8,577,120 | B1* | 11/2013 | Koshti | G06T 7/0004 250/341.8 |
| 8,917,275 | B2* | 12/2014 | Grieves | G06K 9/036 345/467 |
| 8,958,657 | B2* | 2/2015 | Hiraki | G09G 3/2022 382/263 |
| 9,202,145 | B2 | 12/2015 | Guymon | |
| 2003/0012441 | A1* | 1/2003 | Trifonov | G06K 9/4604 382/199 |
| 2004/0061777 | A1* | 4/2004 | Sadok | G08B 17/125 348/83 |
| 2004/0081345 | A1* | 4/2004 | Douglass | G01N 15/1475 382/133 |
| 2004/0175040 | A1* | 9/2004 | Rizzotti | G08B 17/125 382/190 |
| 2005/0069207 | A1* | 3/2005 | Zakrzewski | B64D 45/0015 382/190 |
| 2005/0199323 | A1* | 9/2005 | Nielson | C06B 27/00 149/19.3 |
| 2006/0050925 | A1* | 3/2006 | Mitsubayashi | G07D 7/14 382/100 |
| 2006/0053970 | A1* | 3/2006 | Dreizin | C06B 21/0066 75/354 |
| 2007/0280504 | A1* | 12/2007 | Badawy | G06K 9/00711 382/104 |
| 2008/0075322 | A1* | 3/2008 | Dube | G06K 9/00134 382/100 |
| 2008/0101719 | A1* | 5/2008 | Lim | H04N 1/4072 382/274 |
| 2008/0248578 | A1* | 10/2008 | Deans | C07D 471/14 436/8 |
| 2008/0267493 | A1* | 10/2008 | Ogasawara | G01N 21/783 382/165 |
| 2009/0010486 | A1* | 1/2009 | Merlet | G06K 9/6277 382/100 |
| 2009/0060260 | A1* | 3/2009 | Hou | G06K 9/00771 382/100 |
| 2010/0045789 | A1* | 2/2010 | Fleming | G01N 21/8483 348/79 |
| 2010/0098335 | A1* | 4/2010 | Yamagishi | G08B 17/125 382/168 |
| 2010/0144050 | A1* | 6/2010 | La Grone | G01N 21/766 436/135 |
| 2011/0026791 | A1* | 2/2011 | Collins | G06K 9/62 382/131 |
| 2011/0051993 | A1* | 3/2011 | Caballero | G06K 9/00771 382/100 |
| 2011/0088828 | A1* | 4/2011 | Misek | A61F 13/51496 156/64 |
| 2011/0110602 | A1* | 5/2011 | Hiraki | G09G 3/2022 382/260 |
| 2011/0262109 | A1* | 10/2011 | Schreckenberg | A61B 8/08 386/326 |
| 2012/0045087 | A1* | 2/2012 | Sun | G01N 35/0092 382/100 |
| 2012/0308153 | A1* | 12/2012 | Hwang | G06T 5/002 382/264 |
| 2013/0190206 | A1* | 7/2013 | Leonard | B01L 3/50857 506/9 |
| 2013/0223756 | A1* | 8/2013 | Iketani | H04N 1/393 382/260 |
| 2013/0336586 | A1* | 12/2013 | Moriuchi | G06K 9/4661 382/170 |
| 2014/0153772 | A1 | 6/2014 | Guymon | |
| 2014/0287520 | A1* | 9/2014 | Ghodousi | G01N 21/78 436/164 |
| 2014/0307963 | A1* | 10/2014 | Zimmer | G06T 5/003 382/167 |
| 2014/0321709 | A1* | 10/2014 | Kasahara | B60S 1/0844 382/103 |
| 2016/0091430 | A1* | 3/2016 | Hernandez | G01N 33/227 324/71.1 |

OTHER PUBLICATIONS

Churaman et al ("Initiation and reaction tuning of nanoporous energetic silicon", 2010).*

* cited by examiner

| 0 | 0 | 0 | 0 | 0 | 0 | 0 | 0 | 0 |
|---|---|---|---|---|---|---|---|---|
| 0 | 0 | 0 | 64 | 64 | 64 | 0 | 0 | 0 |
| 0 | 0 | 127 | 127 | 127 | 127 | 127 | 0 | 0 |
| 0 | 64 | 127 | 191 | 191 | 191 | 127 | 64 | 0 |
| 0 | 64 | 127 | 191 | 255 | 191 | 127 | 64 | 0 |
| 0 | 64 | 127 | 191 | 191 | 191 | 127 | 64 | 0 |
| 0 | 0 | 127 | 127 | 127 | 127 | 127 | 0 | 0 |
| 0 | 0 | 0 | 64 | 64 | 64 | 0 | 0 | 0 |
| 0 | 0 | 0 | 0 | 0 | 0 | 0 | 0 | 0 |

Low shape value  High shape value

FIG. 13

SYSTEM AND METHOD OF AUTOMATICALLY DETERMINING MATERIAL REACTION OR SENSITIVITY USING IMAGES

CROSS-REFERENCE TO RELATED APPLICATIONS

This application is a continuation-in-part of U.S. patent application Ser. No. 13/691,450, now U.S. Pat. No. 9,202,145, filed Nov. 30, 2012, entitled "SYSTEM AND METHOD OF DETERMINING MATERIAL REACTION OR SENSITIVITY USING HIGH-SPEED VIDEO FRAMES," which is hereby incorporated by reference herein in its entirety, including but not limited to those portions that specifically appear hereinafter, the incorporation by reference being made with the following exception: In the event that any portion of the above-referenced application is inconsistent with this application, this application supersedes said portion of said above-referenced application.

BACKGROUND

The disclosure relates generally to systems, methods and computer program products for automatically determining whether an energetic substance or a material has experienced a reaction ("go") or a non-reaction ("no-go") during an insult from an impact, friction, ESD or other small-scale sensitivity testing device. Small-scale sensitivity testing is used to determine the risk during storage, transportation or in-process handling, of materials that have pyrotechnic, explosive, or propellant properties.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 8 is an embodiment of a method for evaluating a reaction event of an energetic material illustrating the conversion of pixels in a frame to grayscale in accordance with the teachings and principles of the disclosure;

FIG. 9 is an embodiment of a method for evaluating a reaction event of an energetic material illustrating frames that include a brightness identifier used in accordance with the teachings and principles of the disclosure;

FIG. 13 is an embodiment of a method for evaluating a reaction event of an energetic material illustrating frames that include a color identifier used in accordance with the teachings and principles of the disclosure;

DETAILED DESCRIPTION

Figure 1:
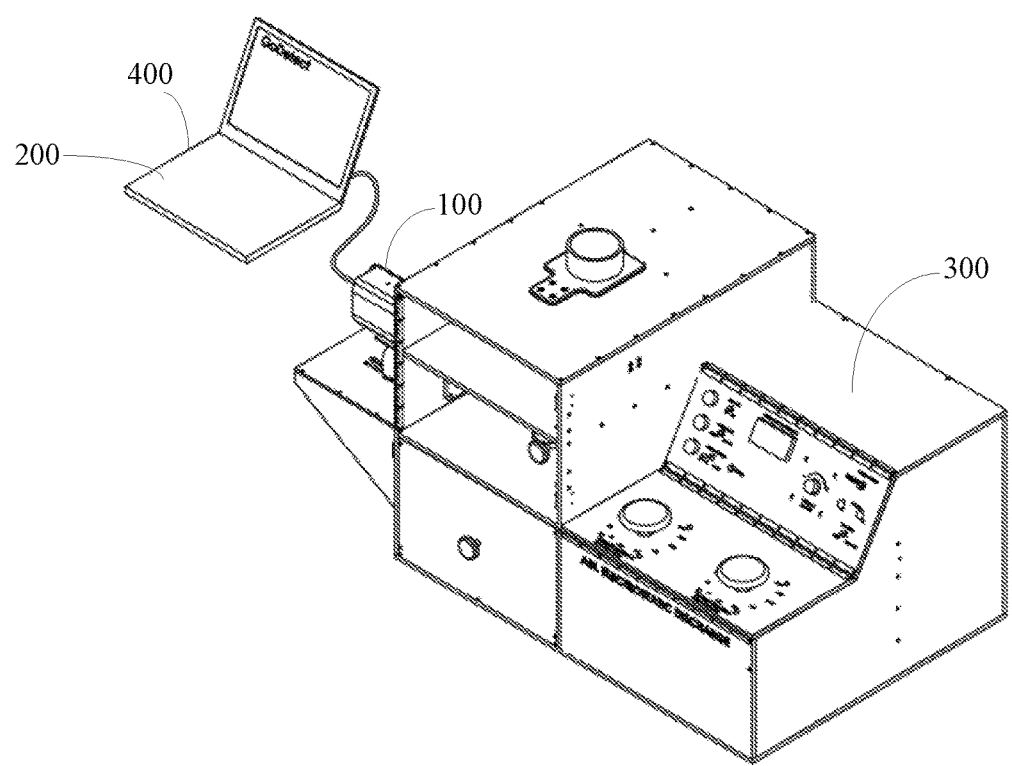
FIG. 1 is a perspective view of an embodiment of a system for evaluating a reaction event of an energetic material made in accordance with the teachings and principles of the disclosure.

In the following description of the disclosure, reference is made to the accompanying drawings, which form a part hereof, and in which is shown by way of illustration specific implementations in which the disclosure is may be practiced. It is understood that other implementations may be utilized and structural changes may be made without departing from the scope of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the present systems, methods, and computer program products for evaluating a reaction event of an energetic material are disclosed and described, it is to be understood that this disclosure is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the phrase "reaction event" refers to a test or series of tests to determine whether a certain energetic material or substance has reacted at a given stimulus level.

Implementations of the systems, devices, and methods disclosed herein may comprise or utilize a special purpose or general-purpose computer including computer hardware, such as, for example, one or more processors and system memory, as discussed in greater detail below. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the following description and claims to refer to particular system components. As one skilled in the art will appreciate, components may be referred to by different names. This document does not intend to distinguish between components that differ in name, but not function.

The disclosure extends to systems, methods and computer program products for automatically determining whether an energetic substance or a material has experienced a reaction ("go") or a non-reaction ("no-go") during an insult from an impact, friction, ESD or other small-scale sensitivity testing device. The systems, methods, and computer program products of the disclosure use a video capturing device, a CPU or computer, sensitivity test equipment, and a set of rules or instructions to be followed for quantifying and determining whether a reaction has occurred or not.

The system may comprise a video capture device, a CPU, software for running a set of instructions or rules as disclosed herein, and sensitivity testing equipment used to determine the reaction (a go or a no-go) of a substance or material. A plurality of images may be captured or collected by the video capture device from a sensitivity test performed on a specific energetic substance or material. The sensitivity test is used to qualify the sensitivity of an energetic substance or material for storage, transportation, or in-process handling. Images taken from the sensitivity test may then be analyzed to determine: (1) which frames are significant, (2) the brightness, buoyancy, shape uniformity, or color of the frames determined to be significant frames, (3) a quantification of the test relative to a background or baseline condition(s), (4) whether the trial resulted in a reaction of the energetic substance (e.g., emits light or smoke), and (5) the Type I error, or likelihood of a false positive, and the Type II error, or likelihood of a false negative, associated with the reaction determination system and method.

It will be appreciated that evaluation of the sensitivity of energetic material (explosives, pyrotechnics, and propellants) is required for transportation, storage, and some in-process scenarios. Specialty sensitivity test equipment may be used to determine whether an energetic material or substance reacts when exerting a force on or imparting energy to a small quantity of the energetic material or substance being tested. Friction, impact, electrostatic discharge (ESD), thermal stimulus, and other scenarios are used to determine whether a reaction will occur at a given stimulus level. If the material reacts at a given stimulus level, the material's chemical structure is changed giving off energy as a byproduct. That energy byproduct may be partitioned into light and sound. Additionally, the chemical byproducts may be seen as hot particulate or gases (smoke).

The disclosure focuses on the light byproduct. Most reactions give off light upon decomposition. The accuracy for reaction detection may be increased, in some instances dramatically, using a camera to capture and record the reaction event and then to further review the result. With the video capture, frames showing a time and spatial progression of the evidence of reaction can be reviewed. However, the determination of whether or not the event can be classified as a reaction (a go) or not (a no-go), is left to the operator or reviewer, unless there is a system and method for quantifying the test results of the reaction event.

The disclosure details a system that quantifies the recorded reaction. The quantified reaction event may then be compared to a threshold to automatically determine whether a reaction was a go or a no-go. Quantifying the reaction event may also enable statistical evaluations of the appropriate threshold to be applied to a given energetic substance or material, as well as tracking of the performance over time of the machine and/or energetic substance or material. The quantified value may be comprised of the value(s) for the event brightness, buoyancy, shape, uniformity, or color.

For example, an electrostatic discharge (ESD) machine is used to impart an electric spark into a small sample. Even if the material does not react, light is generated making it more difficult for an operator, evaluator or reviewer to assess the sensitivity of the material to ESD. Using the system and method of the disclosure, an inert material may be repeatedly (and rapidly) tested to generate an applicable baseline distribution, referred to as a baseline result, of the quantified images of the spark with the inert, non-reacting material. When the energetic or reactive material is tested, the quantified result of the energetic material may be statistically compared to the baseline result to determine whether the material reacted. A threshold value may be toggled by the user to optimize the Type I error and/or the Type II error. Type I error is the probability of a false positive and Type II error the probability of a false negative.

Referring now to FIGS. 1-5, at least one embodiment of a system for evaluating a reaction event of an energetic material is illustrated. The system for evaluating a reaction event of an energetic material may comprise an image capturing device 100, a storage device 200, such as a CPU or computer, at least one sensitivity testing device 300, and a set of instructions 400 that quantify reaction event characteristics. The image capturing device 100 may be used to capture a single or plurality of image frames of the reaction event (illustrated best in FIG. 3). The storage device 200 may be an electronic storage device that may be coupled, or may be in electronic communication, with the image capturing device 100 and may be used to store the plurality of image frames or image data in memory 220.

The image capturing device 100 may be a high-speed video camera. In an embodiment, the high-speed video camera may be capable of recording and capturing at least 1,000 frames per second (fps). However, it will be appreciated that any imaging device that is capable of recording and capturing video, whether at a rate that is more or less than 1,000 fps, may be utilized by, and falls within the scope of, the disclosure.

The storage device 200 may be coupled or electronically connected to the image capturing device via a wired communication device or system or a wireless communication or transmission system. For example, an electronic and/or physical tether may be used for communication purposes between the image capturing device 100 and the storage device 200. Examples of wireless communications or transmissions, include, but are not limited to, Wi-Fi, Bluetooth, infrared, or other forms of wireless non-tethered connectivity for providing communication between the image capturing device 100 and the storage device 200. It will be appreciated that radio frequency from any available spectrum, infrared of all configurations, ultrasonic, and optical may be used for communication purposes between the image capturing device 100 and the storage device 200.

Figure 2:
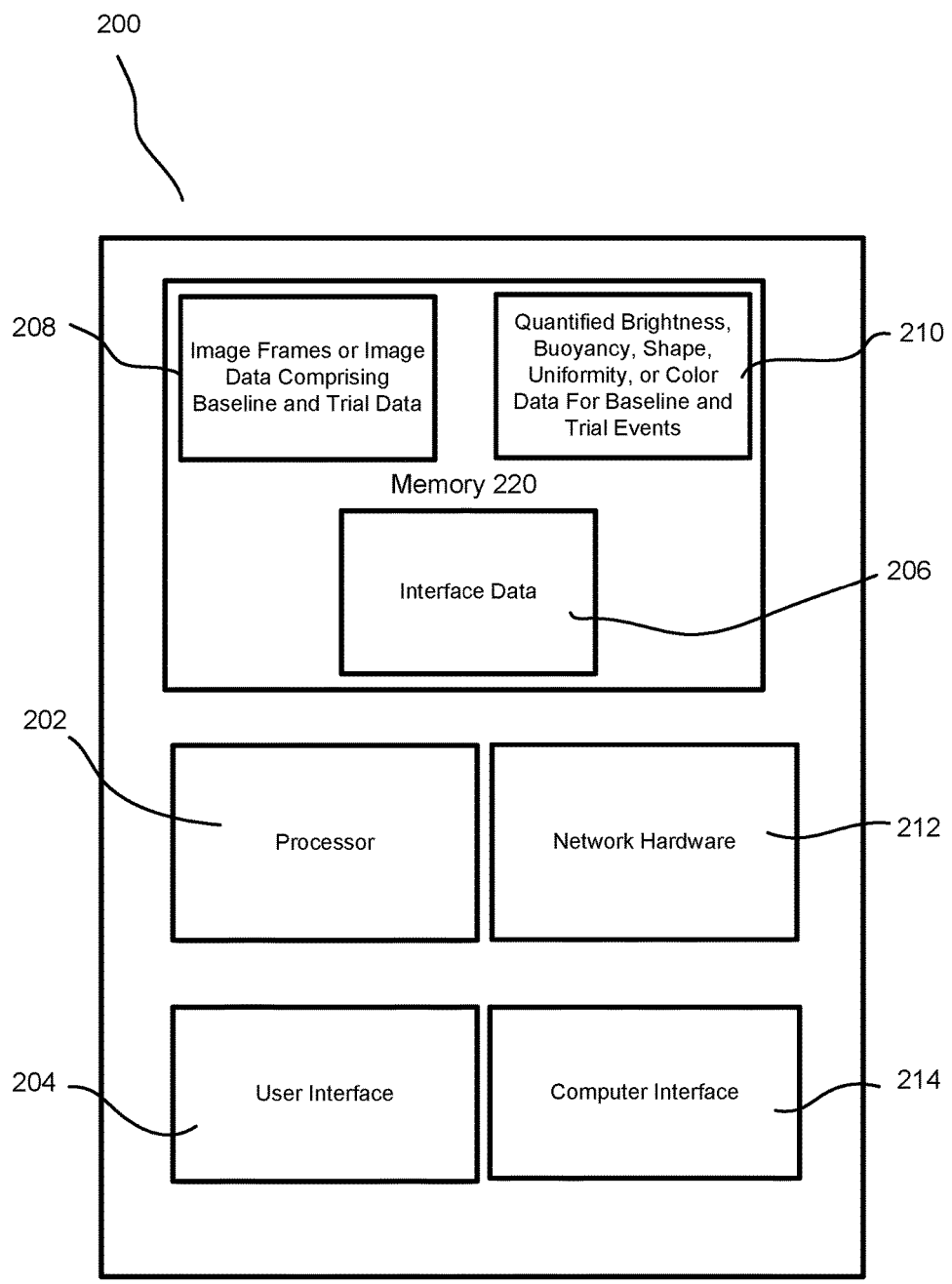
FIG. 2 is an illustration of an embodiment of a hardware—software schematic in accordance with the teachings and principles of the disclosure.

Referring specifically to FIG. 2, it will be appreciated that the storage device 200 may include electronic storage, memory, a CPU or a combination of the above for processing the plurality of image frames. A computer processor 202 may be used to act as a central processing unit that may be configured to operate according to instructions provided by firmware and software. The storage device may comprise a user interface 204 thereby allowing a user to operate the image capturing device 100 using software, as well as interacting with the storage device 200. The user interface 204 may be comprised of display devices that provide visual cues to a user. The user interface 204 may also provide audio and tactile cues to users who need or prefer something other than sight cues. Data generated and used in conjunction with the user interface 204 may be stored in memory 220 as an interface data set 206. The images and data generated from the imaging device 100 used in conjunction with the sensitivity testing device 300 may be stored in memory 220 as image frames or image data 208, which may include a baseline data set and a trial data set. The image data 208 may be processed and read from memory 220 by the processor 202 and processed for a desired output and stored to memory 220. It will be appreciated that the processor is capable of reading data from memory and writing data to memory as is common in computing devices. The quantified brightness, buoyancy, shape, uniformity, or color data 210 for baseline and trial events may also be stored in memory 220 and used for statistical evaluation and analysis.

The storage device 200 or the imaging device 100 may comprise network hardware 212 for facilitating a data connection over networks, such as the internet. The network hardware 212 may facilitate communication with a connected imaging device, computing device, such as a personal computer, a tablet device, or a mobile phone. Any such connection between the storage device 200 or the image device 100 and the aforementioned peripheral computing devices may be utilized by the disclosure, and the connection could be physical with a data cable, or wireless, such as Wi-Fi, blue tooth or other wireless transmissions. To further facilitate use with computer like peripherals, the storage device 200 or the imaging device 100 may further comprise various computer interfaces 214, such as ports and complementary firmware and software as is common in the art. It will be appreciated that the storage device 200 may be any type of desktop computer, laptop computer, a tablet device, PDA, mobile telephones or other computing device that is capable of processing image frames.

The at least one sensitivity testing device 300 may be used for conducting a sensitivity test, such as a friction, impact, electrostatic discharge (ESD), and thermal stimulus test with respect to the energetic material or substance. It will be appreciated that the CPU of the storage device 200 may be used to run a set of computer readable instructions that quantify a plurality of reaction event characteristics, wherein the instructions comprise calculating brightness, buoyancy, shape, uniformity, or color of the reaction event. The CPU may also be used to run a set of computer readable instructions for statistical evaluation and analysis.

Figure 3:
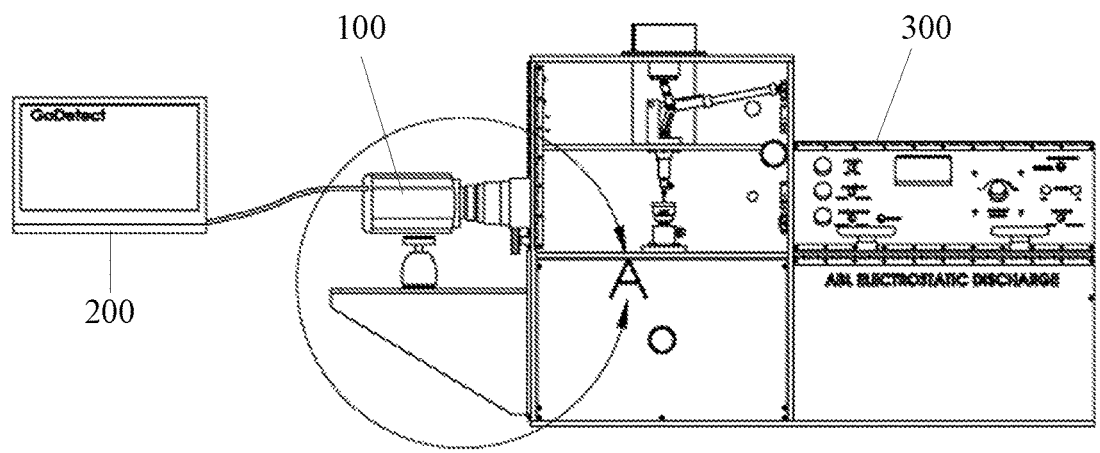
FIG. 3 is a front view of an embodiment of the system for evaluating a reaction event of an energetic material illustrating sensitivity test equipment made in accordance with the teachings and principles of the disclosure.
Figure 4:
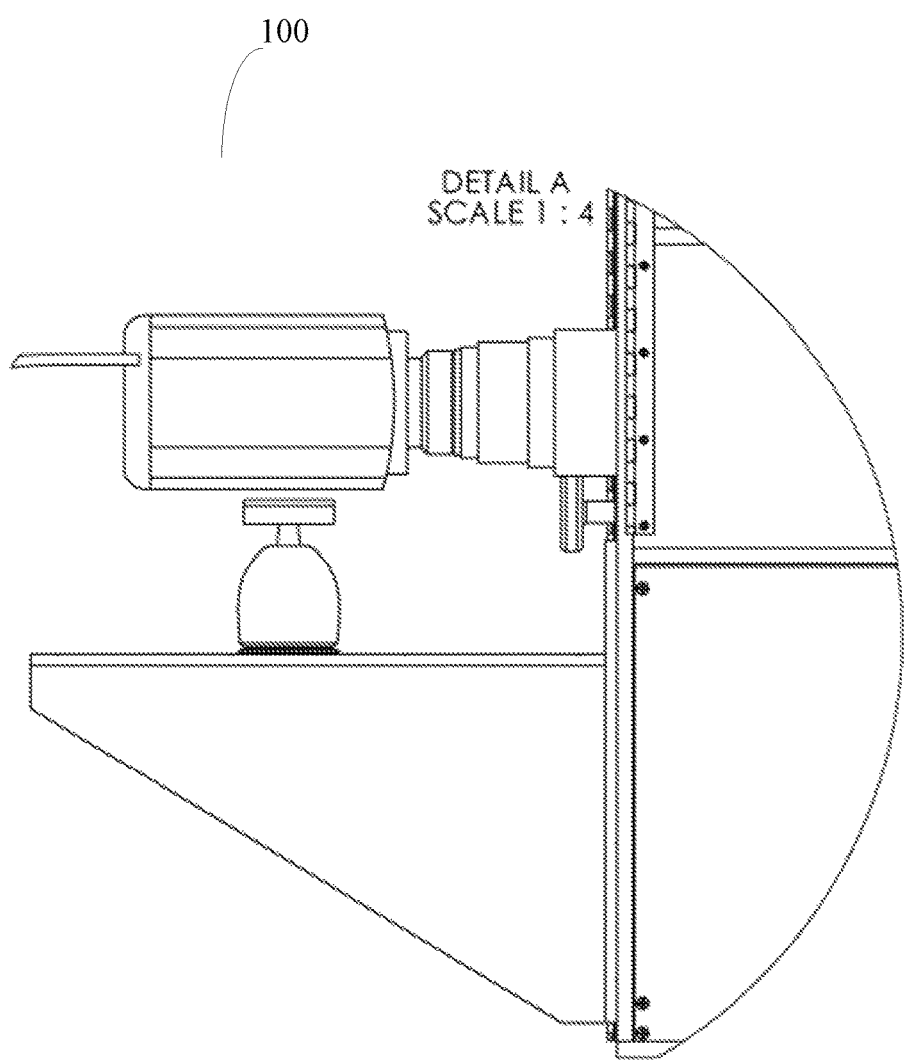
FIG. 4 is an enlarged view of the Detail A illustrated in FIG. 3 of an embodiment of the system for evaluating a reaction event of an energetic material made in accordance with the teachings and principles of the disclosure.
Figure 5:
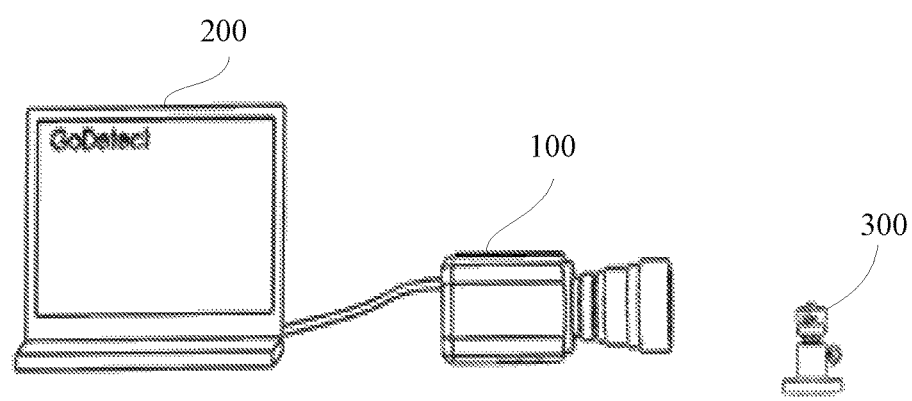
FIG. 5 is a front view of an embodiment of a system for evaluating a reaction event of an energetic material made in accordance with the teachings and principles of the disclosure.

FIGS. 1-5 illustrate at least one testing scenario, wherein the system for evaluating a reaction event of an energetic material is in operation. FIG. 1 is a perspective view of an embodiment of the system for evaluating a reaction event of an energetic material. FIG. 2 illustrates a schematic of a storage device 200 having a computer processor that may be used to act as a central processing unit that may be configured to operate according to instructions provided by firmware and software, which may be used to quantify the plurality of frames or image data (as discussed more fully below) as well as for statistical evaluation and analysis. FIG. 3 is a front view of an embodiment of the system for evaluating a reaction event of an energetic material illustrating sensitivity test equipment. FIG. 4 is an enlarged view of "Detail A" illustrated in FIG. 3 of an embodiment of the system for evaluating a reaction event of an energetic material. FIG. 5 is a front view of an embodiment of a system for evaluating a reaction event of an energetic material.

Figure 6:
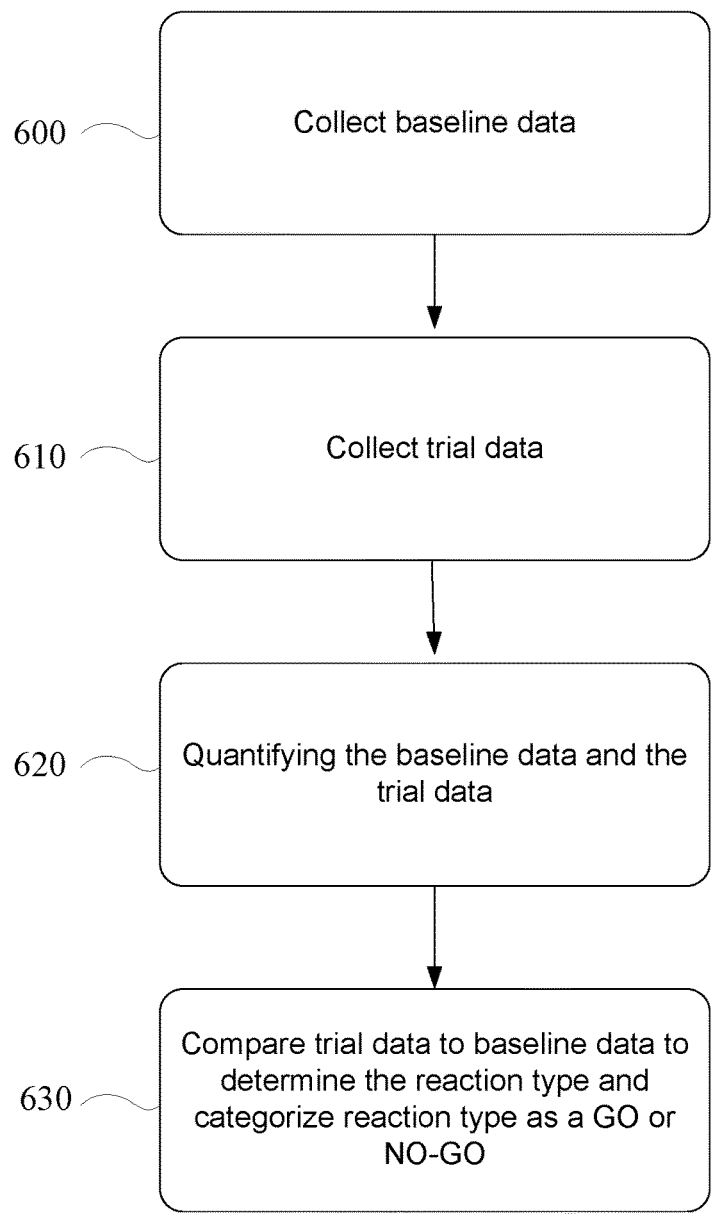
FIG. 6 is a flow diagram of an embodiment of a method for evaluating a reaction event of an energetic material in accordance with the teachings and principles of the disclosure.

Referring now to FIG. 6, an embodiment of a method for evaluating a reaction event of an energetic material is illustrated, and may comprise several individual steps or processes. At 600 a series or plurality of images may be collected using the image capturing device 100 of a baseline reaction test or event and the baseline data may be recorded, collected, and stored on a storage device, such as a computer. The capturing of the single or plurality of image frames of the baseline reaction test may be completed using an image capturing device 100 described above. A baseline data set may be obtained from the baseline reaction test or event. The baseline data set may include information relating to the current testing conditions in a given space or area and may be used to compare against a trial data set to assist in determining whether a go or no-go reaction has occurred. It will be appreciated that when performing a baseline reaction test using one or more sensitivity test devices, not all of the information relating to the energetic material may be present during the baseline reaction test or event. It will be appreciated that some of the information relating to the energetic material may be present during the test such that a true baseline test under existing conditions may be run and data obtained.

At 610, a series or plurality of images may be collected using an image capturing device 100 of a trial reaction test or event and the trial data may be recorded, collected, and stored on the storage device. The capturing of a plurality of image frames of the trial reaction test or event may be completed using the image capturing device 100. A trial data set may be obtained from the trial reaction test or event. The trial data set may include information relating to the specific energetic material being tested. It will be appreciated that the process of performing a trial reaction test requires the use of one or more sensitivity test devices 300 where the energetic material is present during the trial reaction test and the information and data relating to the test is recorded and captured.

Thus, the method may include collecting a series of image frames, which contain and may be identified as "frames of interest" from the baseline reaction event and from the trial reaction events. As noted above, the image capturing device 100 may be a high-speed video camera and may include a trigger to begin the capture event. It will be appreciated that the trigger may be an image based trigger or could be any other trigger known in the art or that may become known in the art for actuating an image capturing device, thereby starting an image capturing session for capturing image frames from a baseline or trial reaction test or event. Each test for the baseline reaction event and the trial reaction event (i.e., testing of the energetic substance or material of interest) may be completed while recording and capturing data relating specifically to the reaction event.

At 620, the baseline data set and the trial data set may be quantified for statistical evaluation and analysis. Quantifying the baseline data set and the trial data set may comprise the following: calculating the brightness of the baseline reaction test and the trial reaction test and storing the results in memory; calculating the buoyancy of the baseline reaction test and the trial reaction test and storing the results in memory; calculating the shape of the baseline reaction test and the trial reaction test and storing the results in memory; calculating the uniformity of the baseline reaction test and the trial reaction test and storing the results in memory; and calculating the color of the baseline reaction test and the trial reaction test and storing the results in memory.

At 630, the quantified trial data set may be processed by a processor and compared to the quantified baseline data set, such that a determination may be made as to whether a reaction event occurred based on the comparison of the quantified trial data set to the quantified baseline data set.

Referring to FIGS. 7-15, an embodiment of a method for evaluating a reaction event of an energetic material is illustrated, and may comprise several individual steps or processes. The overall process includes capturing and collecting the baseline data and the trial data and storing the results in memory as noted above with respect to FIG. 6. The baseline and trial data may include a plurality of image frames that may be stored in memory. The image frames that indicate a change in an image property, such as a change in brightness, buoyancy, shape, uniformity, or color, may be considered for the statistical analysis of whether a reaction is classified as go reaction or a no-go reaction. After the baseline data and the trial data are captured, collected and stored in memory, the baseline data and the trial data may then be processed by the processor and quantified for objective evaluation and analysis. The trial data may be compared to the baseline data to determine and classify the reaction type, either as a go reaction or no-go reaction.

Figure 7:
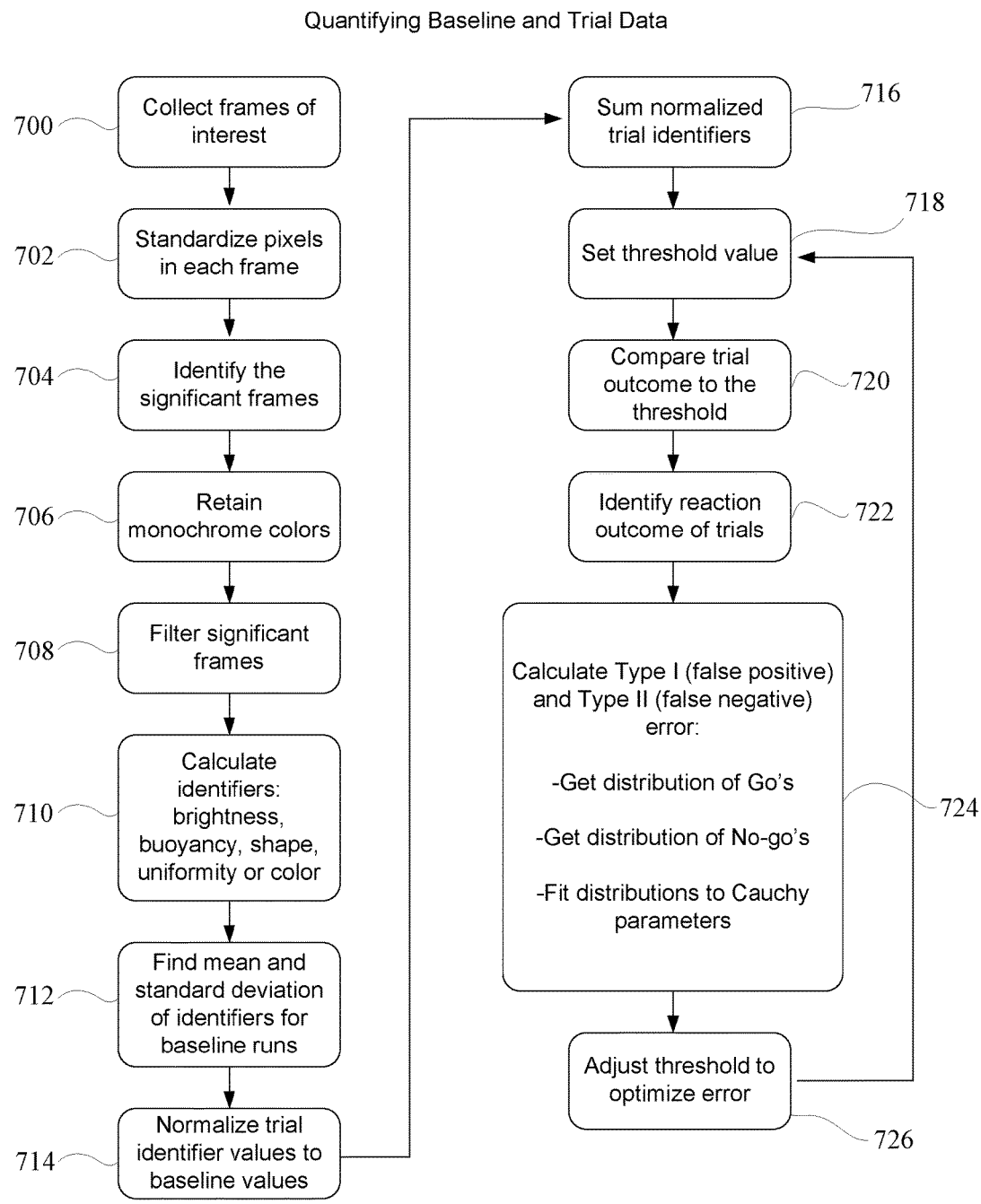
FIG. 7 is a flow diagram of an embodiment of a method for evaluating a reaction event of an energetic material in accordance with the teachings and principles of the disclosure.

More specifically and referring to FIG. 7, the method may include collecting the frames of interest by capturing a plurality of image frames of a baseline reaction event using the image capturing device 100. The baseline data set may be obtained from the baseline reaction event and the baseline data set may not comprise all of the information of the energetic material. The baseline data set, including the plurality of image frames of the baseline reaction event, may be stored in computer readable memory.

Collecting the frames of interest may also include capturing a plurality of image frames of a trial reaction event using the image capturing device 100. The trial data set may be obtained from the trial reaction event and the trial data set may comprise information relating to the energetic material. The trial data set, including the plurality of image frames of the trial reaction event, may be stored in computer readable memory.

It will be appreciated that capturing of the reaction event may include a trigger to begin the capture event or session. It will be appreciated that the trigger may be an image based trigger or the trigger may be any other trigger known in the art or that may become known in the art for starting an image capturing device to capture image frames from a baseline or trial reaction test or event. Each test for the baseline reaction event and the trial reaction event (i.e., testing of the energetic substance or material of interest) is completed while recording and capturing data relating specifically to the reaction event.

The method may comprise quantifying the baseline data set and the trial data set. The quantifying process may further comprise using the following identifiers: calculating brightness from the plurality of image frames of the baseline reaction event and the trial reaction event and storing the results in memory; calculating the buoyancy from the plurality of image frames of the baseline reaction event and the trial reaction event and storing the results in memory; calculating the shape from the plurality of image frames of the baseline reaction event and the trial reaction event and storing the results in memory; calculating the uniformity from the plurality of image frames of the baseline reaction event and the trial reaction event and storing the results in memory; and calculating the color from the plurality of image frames of the baseline reaction event and the trial reaction event and storing the results in memory. The quantified trial data set may be compared to the quantified baseline data set. A determination may be made as to whether a reaction event occurred based on the comparison of the quantified trial data set to the quantified baseline data set.

Once the baseline data set and the trial data set is obtained at 700, the process of quantifying the data collected for the baseline reaction event and the trial reaction event may comprise the following.

At 702, in each of the frames of interest, all of the pixels may be standardized. The standardization process may use a brightness or color value to eliminate the visual effects of the ambient surroundings. Ambient surroundings include all the items in the frame that support the test, but are not integral in determining the reaction outcome. For example, in an ESD test, the brightness value may simply be reduced so that only the spark is evident and the surrounding objects are not visible. This standardization process may be automatically completed by the storage device 200, such as a computer, and a set of computer readable instructions or rules.

At 704, the frames of interest may be analyzed for an indication of a change obtained during the baseline reaction event and the trial reaction event. The frames of interest that indicate such a change may be separated from the frames of interest where there is no indication of such a change. The separated frames of interest may be labeled or otherwise identified as "significant frames." It will be appreciated that the change in the frames of interest may be a change in an image property, such that a frame may be labeled or otherwise identified as a significant frame when there is a change in the image property. For example, changes in the image property may include, but are not limited to, additional light or scattered light or a change in the size or shape of the lighted object.

A background map may be created for each of the significant frames. The background map may be created by standardizing all pixels in each of the significant frames to a baseline brightness value to thereby eliminate all visual effects of the ambient surroundings, such that the analysis is focused directly on an analysis site. When brightness is being analyzed, each of the frames of interest may be analyzed and compared to an average brightness as part of the standardization process. A frame may be labeled or otherwise identified as a significant frame when its brightness is more than 1-10 standard deviations greater than a mean brightness.

At 706, the blue, green, and red components of each significant frame are retained in memory to be used to identify color differences or to convert the color to a grayscale image. The conversion to grayscale may be advantageous because it may increase the speed of, and simplify, the process. Additionally, brightness may be easily determined using a grayscale image. At 708, each of the grayscale or monochrome color images may be filtered to eliminate any extraneous, unrelated or otherwise unwanted image properties or changes. The process of filtering may include weighting the filter by giving each pixel a grayscale brightness value. The filtering may be centered on the brightest part of the grayscale image and then the grayscale brightness value is attenuated as a distance from a center of a brightest point increases (illustrated best in FIG. 8). Thus, a brightness value may be assigned to each pixel in each of the significant frames, wherein the brightness value for a given significant frame may be the sum of all pixel values in that significant frame normalized by the resolution and the number of significant frames identified in the baseline reaction event or the trial reaction event, or may be the sum of the pixel values for each frame weighted in a power-law method for each successive frame, or may be the maximum of the sum of the pixel values of the most significant or pronounced frame.

For example, as illustrated in FIG. 8, the brightest grayscale value illustrated is the center pixel of a 9×9 resolution image and that pixel has a value of 255. As the distance from the brightest part of the image (i.e., the center pixel) increases, the brightness value is attenuated, such that the grayscale value of the dimmest pixel, still having a brightness value, is 64 in the example in FIG. 8. An assigned pixel brightness value of 0 illustrates a black or non-bright pixel. It will be appreciated that the attenuation may be non-linear and may follow a hyperbolic tangent distribution.

The disclosure may utilize one or more identifiers or qualifiers to ultimately yield a single identifying value, which may reflect or represent a difference between the trial reaction event and the baseline reaction event for qualitative and statistical analysis. The identifiers may comprise:

brightness, buoyancy, shape, uniformity, or color. At 710, each of the identifiers may be calculated and a value assigned or provided.

Figure 9:
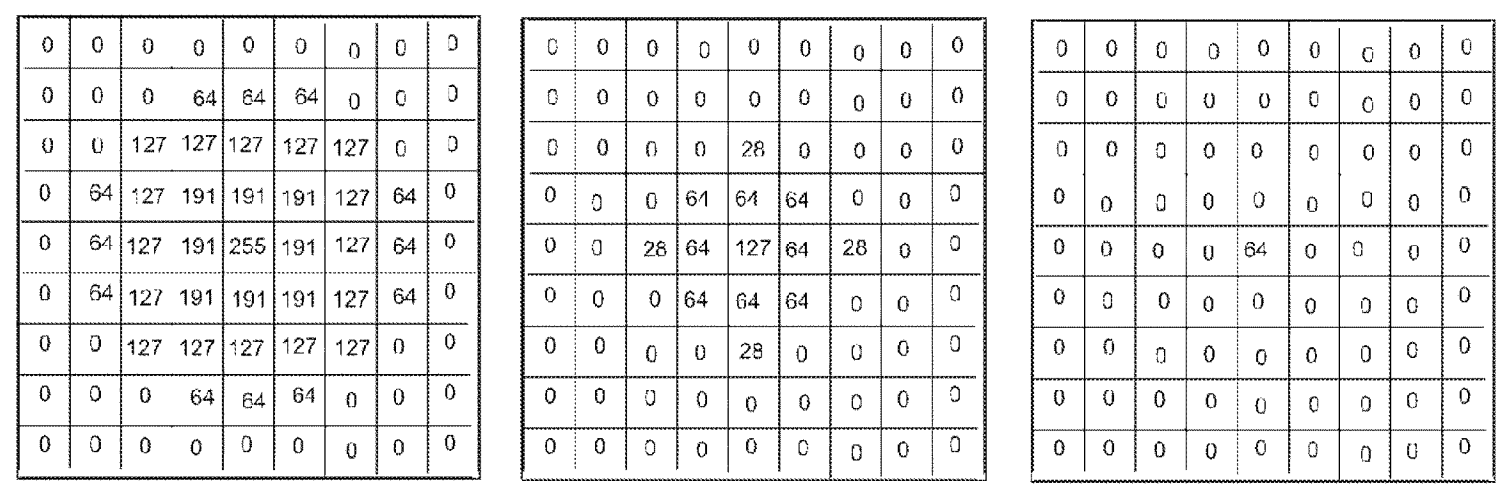

Referring to FIG. 9, the brightness identifier of a significant frame or image may be calculated and a value assigned. The brightness value may be calculated from the sum of the assigned pixel values for each significant frame, normalized by the number of significant frames being considered and the resolution, or may be the sum of the pixel values for each frame weighted by the successive frame number, or may be the maximum of the sum of the pixel values of the most significant or pronounced frame. Using a simplified example illustrated in FIG. 9, the sum of the assigned pixel values for each significant frame is as follows: 4583 for frame 1+751 for frame 2+64 for frame 3, which summed is equal to 5398. The 5398 value may be normalized by dividing that value by the number of significant frames being analyzed, in this simplified example 3 frames are analyzed, which is equal to 1799. The resulting value is then divided by the resolution, which in FIG. 9 is 9 pixels×9 pixels or 81, to obtain the brightness value of 22.21 or a value proportional to such. The brightness value may also be the maximum of any of the significant frames normalized by the resolution so 4583/81=56.58, or a value proportional to such. The brightness value may also be found from the sum of the pixel values for each frame weighted by the successive frame number normalized by the resolution, e.g. 4583*1+751*2+64*3=6277/81=77.5, or a value proportional to such.

Figure 10:
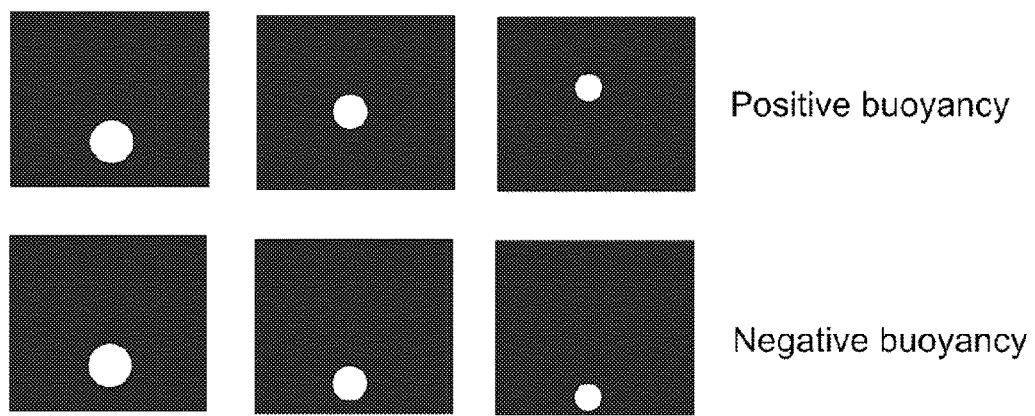
FIG. 10 is an embodiment of a method for evaluating a reaction event of an energetic material illustrating frames that include a buoyancy identifier used in accordance with the teachings and principles of the disclosure.

Referring to FIG. 10, the buoyancy identifier of a significant frame or image may be calculated and a value assigned. The buoyancy value may be determined from the difference between the average center of mass (based on the grayscale or other monochrome pixel value) and the value of the center of mass for the first significant frame. In the figure, there is shown two sets of significant frames for illustration purposes. The top row illustrates three significant frames that may be classified as having positive buoyancy. The bottom row illustrates three significant frames that may be classified as having negative buoyancy. The first significant frame in each row is the frame on the far left of the page.

Figure 11:
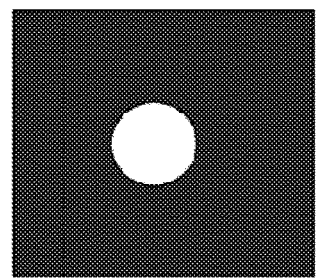
FIG. 11 is an embodiment of a method for evaluating a reaction event of an energetic material illustrating frames that include a shape identifier used in accordance with the teachings and principles of the disclosure.
Figure 11:
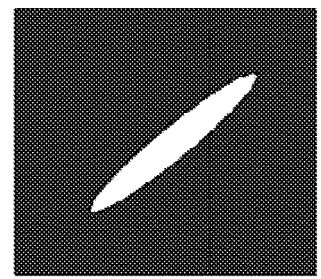

Referring to FIG. 11, the shape identifier of a significant frame or image may be calculated and assigned a value. The shape may be identified or found using linear algebra to weight each frame's shape by performing matrix multiplication with the pixel matrix and a weighting matrix, minus the product of the brightness and center of mass in the horizontal and vertical directions. The shape identified or found from the matrix multiplication can yield a measure of the ratio of the length to the width. For example, the illustration on the left of FIG. 11 represents a low shape value having a value of 1, since the length and width are equal. The illustration on the right of FIG. 11 represents a high shape value having a value greater than 1, since the length is much larger than the width. The resulting value may be normalized and summed over all of the significant frames.

Figure 12:
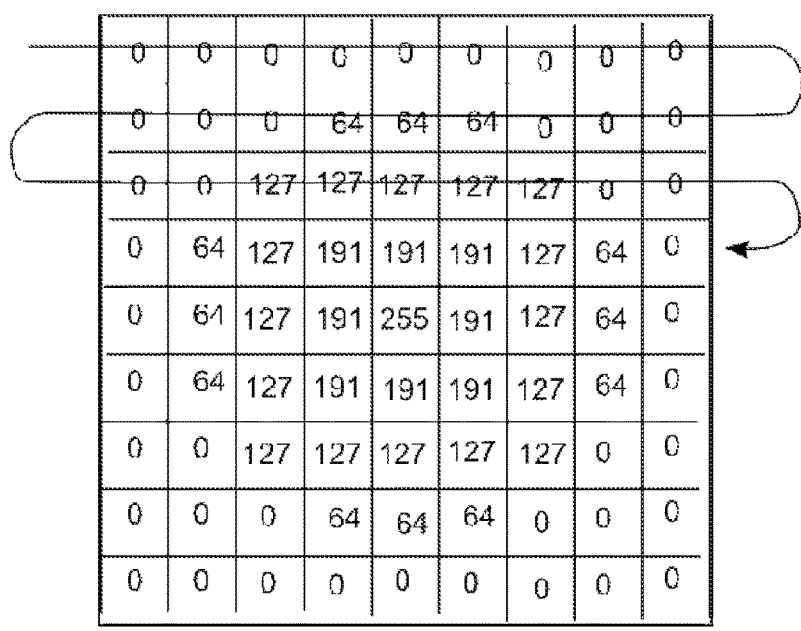
FIG. 12 is an embodiment of a method for evaluating a reaction event of an energetic material illustrating frames that include a uniformity identifier used in accordance with the teachings and principles of the disclosure.

Referring to FIG. 12, the uniformity identifier of a significant frame or image may be calculated and assigned a value. The uniformity may be found by reducing the illustrated matrix to an array and then counting the peaks in the values as if they were a profile. This may be accomplished row-by-row as illustrated. In other words, uniformity may be found from a reshaped pixel matrix, where the number of peaks of the reshaped array is found, summed and then normalized. In the figure, the 1st or top row will have no corresponding peak because the pixel values are all 0. Conversely, rows 2 and 8, rows, 3 and 7, and rows 4 and 6 will have the same or similar peaks.

Figure 13:
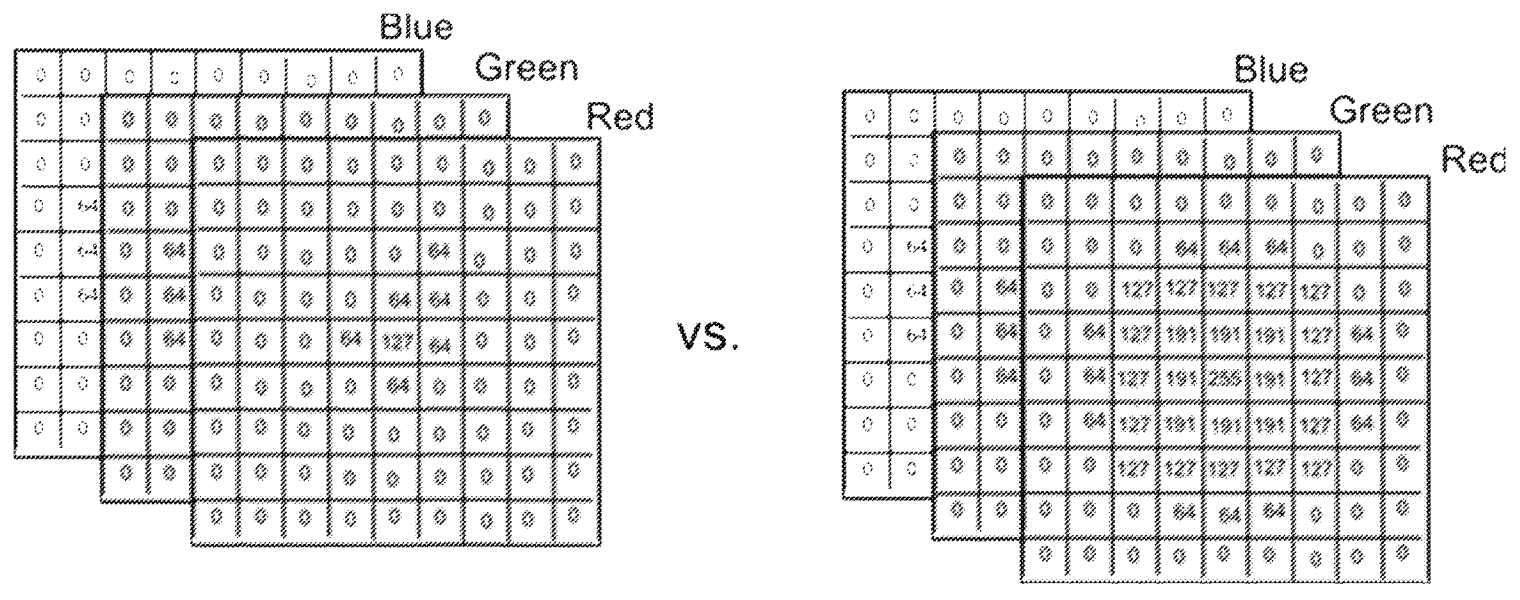

Referring to FIG. 13, the color identifier of a significant frame or image may be calculated and assigned a value. The color may be found by calculating the ratio of the sum of the red, blue, green pixels or linear combination thereof for each frame and the total brightness which can be a sum of a linear combination of the red, blue, and green pixels. That color ratio can be then summed over all the significant frames and normalized by the resolution. In the figure, the collection of matrices on the left is an example of the blue, green, and red components of one frame. The blue and green matrices each sum to 4774 whereas the red matrix on the left sums to 511, thus the fraction of red is 511/(511+4774+4774)=0.051, whereas for the image on the right all of the matrices of pixels sums to 4774 and thus the fraction of red in the image is 4774/(4774+4774+4774)=0.33.

Referring back to FIG. 7, at 712 the mean baseline value and the standard deviation for the baseline reaction event for each identifier may be found and the results may be stored in computer readable memory or listed in a summary file.

At 714, the value for the trial reaction event may be found by normalizing each identifier of brightness, buoyancy, shape, uniformity, or color for the trial reaction event and assigning a value to each identifier. To obtain the normalized value, the mean baseline value is subtracted from the trial identifier's value and then divided by the baseline standard deviation for that identifier, such that normalizing is based on the mean baseline value and the standard deviation for brightness, buoyancy, shape, uniformity, or color of the baseline reaction event.

At 716, the normalized value of each identifier is combined to yield a single identifying value that reflects a difference between the trial reaction event and the baseline reaction event. The identifying value may be determined from the summation of one or all the trial identifiers of brightness, buoyancy, shape, uniformity, and color and thus the identifying value can be proportional to the number of standard deviations from the baseline values.

At 718, a threshold value may be specified and set. A specified threshold value may be set to determine whether a reaction event falls within predetermined parameters characterizing the reaction event as a go or no-go reaction. At 720, the identifying value of the trial outcome may be compared to the specified threshold. At 722, the reaction outcome of the trials may be identified. If the identifying value of the trial identifiers of the reaction event is greater than the specified threshold, the trial is then designated as a go reaction. Conversely, if the identifying value of the trial identifiers of the reaction event is less than the specified threshold, the trial is then designated as a no-go reaction (illustrated best in FIG. 14).

At 724, the method may further comprise calculating Type I error (likelihood of a false positive) and Type II error (likelihood of a false negative) for the specified threshold. A recursive method may be used to calculate or estimate the Type I error and Type II error, wherein the distribution of the identifying value of the trial identifiers for the go reactions and the distribution of the identifying value of the trial identifiers for the no-go reactions may be located in a continuous probability distribution.

Figure 14:
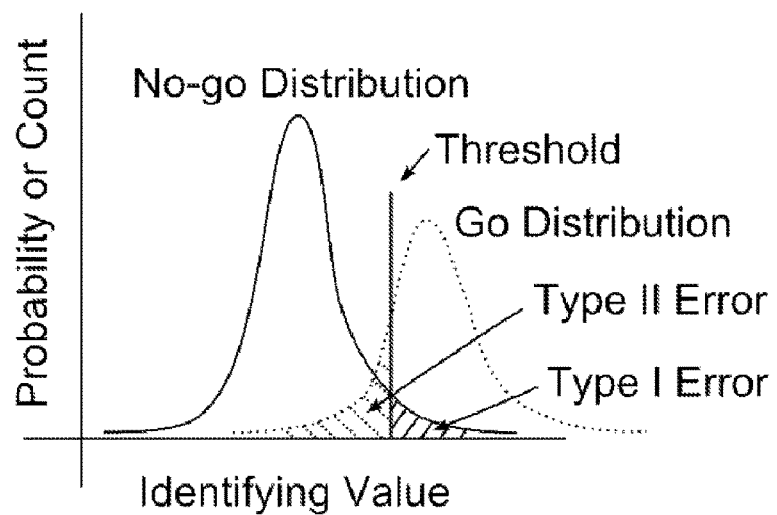
FIG. 14 is an embodiment of a method for evaluating a reaction event of an energetic material illustrating a continuous probability go distribution, a continuous probability no-go distribution, a threshold and Type I and Type II errors in accordance with the teachings and principles of the disclosure.

Referring now to FIG. 14, the distribution of the trial values for the go reactions (found from the trial events with values greater than the threshold) and the distribution of the no-go reactions (values less than the threshold) may both be fitted to a Cauchy distribution. The Cauchy distribution may be used because the tails of the distribution better represent the observed data, there are only 3 variables that describe the distribution, and it is efficiently implemented.

It will be appreciated that there may be false positives (Type I error) in the estimated go distribution and false negatives (Type II error) in the estimated no-go distribution. The estimate for the Type II error may be accomplished by assuming that the number of go reaction values (in a given interval of values defining a go reaction) includes a portion of no-go reaction values, and the estimate for the Type I error may be accomplished by assuming that the number of no-go reaction values (in a given interval of values defining a no-go reaction) includes a portion of go reaction values (illustrated best in FIG. 14). The Type II error is illustrated in FIG. 14 as the shaded portion under the curve and to the left of the threshold, while the Type I error is illustrated as the shaded portion under the curve to the right of the threshold.

Figure 15:
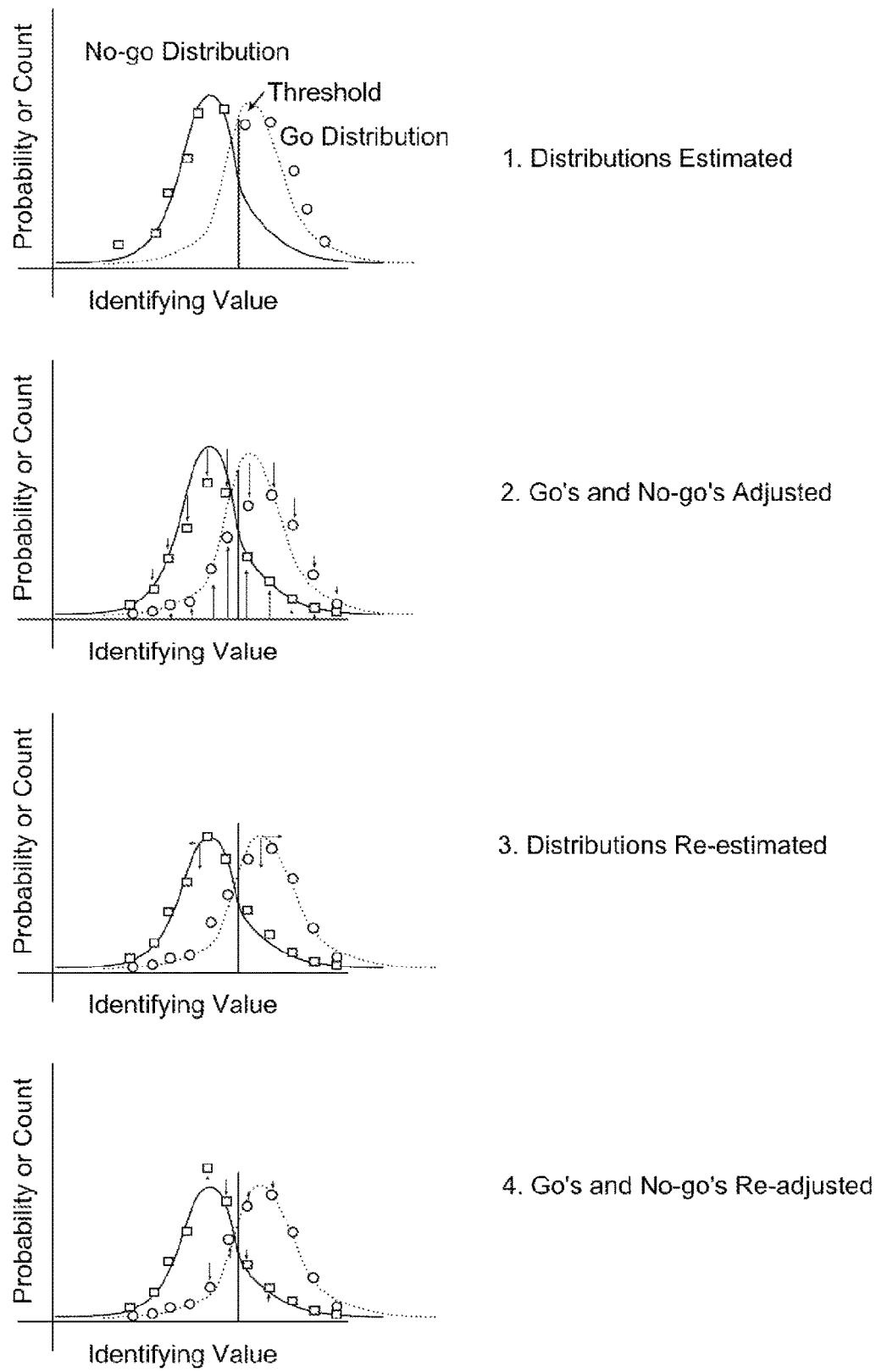
FIG. 15 is an embodiment of a method for evaluating a reaction event of an energetic material illustrating the estimated go and no-go distributions, the adjusted go and no-go count or likelihood, the re-estimated go and no-go distributions, and the re-adjusted go and no-go count or likelihood in accordance with the teachings and principles of the disclosure.

Referring now to FIG. 15, the proportion of no-go reactions in the go count or distribution can be estimated from the no-go distribution value at that interval. The number of go reactions or the probability of a go reaction in that interval may then be adjusted down (to account for the number of no-go reactions incorrectly classified as a go reaction). The Cauchy distribution estimate may then be re-estimated for both distributions based on the updated count or probability of no-go reactions and go reactions. This process is recursively completed to convergence.

The Type I error or false positive likelihood can then be estimated by the proportion of the no-go distribution that is greater than the threshold value. In a similar manner, the Type II error or false negative likelihood can be estimated by the go distribution fraction less than the threshold. If the trial outcome is greater than the specified threshold, the trial is designated a go reaction. If the trial outcome is less than the specified threshold, the trial is designated a no-go reaction.

After the initial go and no-go distributions are estimated, the method may comprise adjusting the go and no-go distribution. A portion of the reactions identified as go reactions to no-go reactions based on the estimated probabilities of go reactions and no-go reactions at a given identifying value or collection of identifying values may be reclassified or re-estimated. Similarly, the process may also comprise reclassifying or re-estimating a portion of the reactions identified as no-go reactions to go reactions based on the estimated probabilities of go reactions and no-go reactions at a given identifying value or collection of identifying values. This process is recursively completed to convergence.

It will be appreciated that the value of the Type I error or the Type II error may be optimized by changing the threshold value to reflect the appropriate amount of risk obtained by the sensitivity test results. At 726, the threshold may be adjusted to optimize the Type I or Type II error. Adjust the threshold to optimize the Type I and/or Type II error. If the desire is to minimize the risk during handling, storage, or transportation then minimization of the false negatives would be an objective; however with minimization of the Type II error, the Type I error or false positive likelihood increases. The trade-off between the magnitudes of the likelihood of Type I or Type II error can be optimized to minimize the risk to personnel during operations, storage, and transportation while not being unrealistically cautious.

It will be appreciated that the above method may be a set of computer readable instructions or rules to automate the process, such that the results and outcomes of the test are quickly and efficiently provided as output to a user. The user may then use the information to make a qualitative determination of whether a reaction event should be classified as a go reaction or a no-go reaction. Thus, because of the automation of the process disclosed herein, the process may be repeated at various sites in many different locations, thereby providing predictability on an objective basis.

Figure 16:
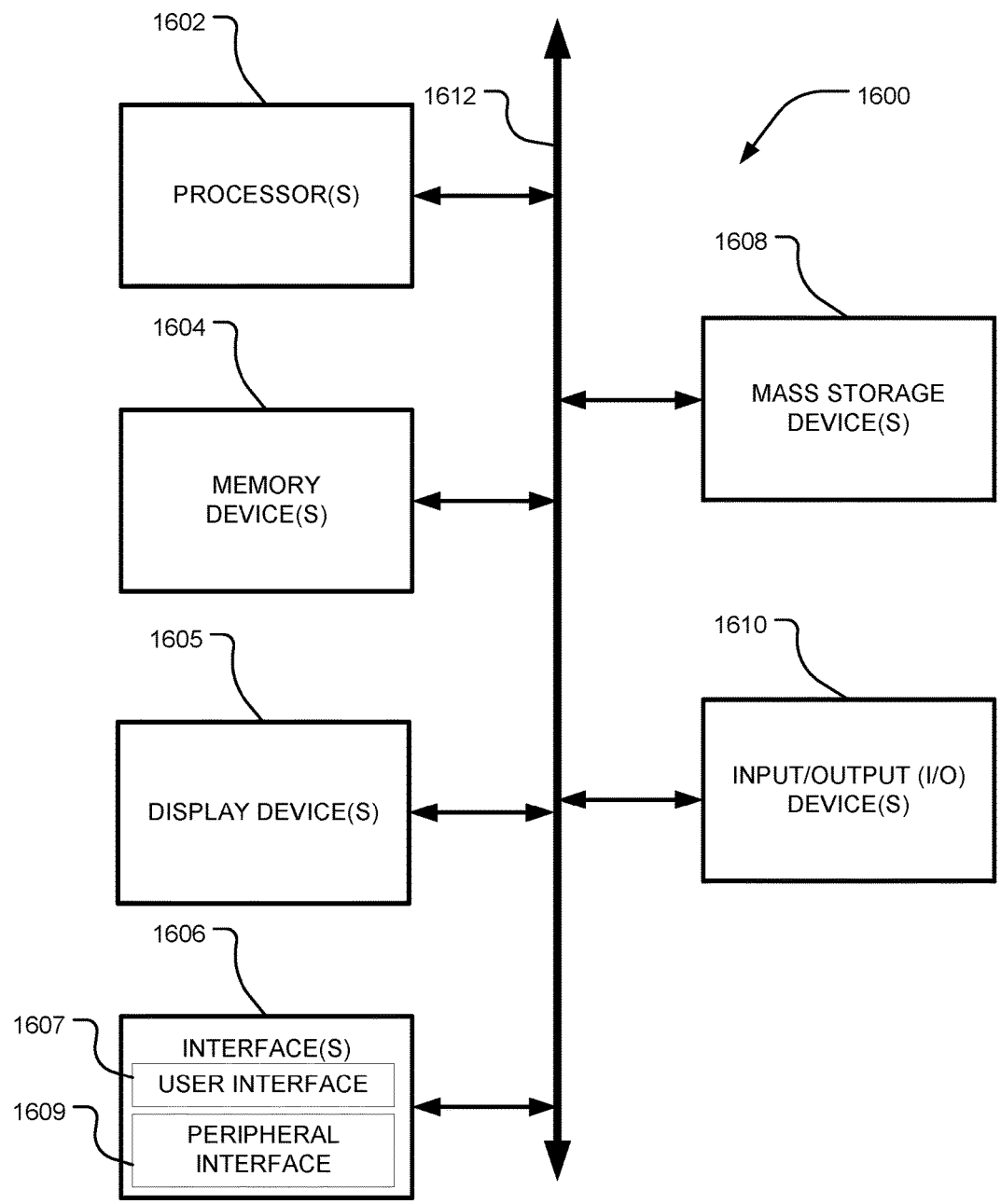
FIG. 16 is a block diagram depicting an example computing device consistent with the enabling disclosure of the computer processes taught herein.

FIG. 16 is a block diagram depicting an example computing device 1600. In some embodiments, the computing device 1600 may be used to perform various procedures, such as those discussed herein, or may be used to implement one or more of the systems and components discussed herein. For example, computing device 1600 may allow a user or administrator to access and use the computer program products disclosed herein. Further, computing device 1600 may interact with any of the systems and components described herein. Accordingly, computing device 1600 may be used to perform various procedures and tasks, such as those discussed herein. Computing device 1600 can function as a server, a client or any other computing entity. Computing device 1600 can perform various functions as discussed herein, and can execute one or more application programs, such as the application programs described herein. Computing device 1600 can be any of a wide variety of computing devices, such as a desktop computer, a notebook computer, a server computer, a handheld computer, a smart phone, a tablet, and the like.

Computing device 1600 includes one or more processor(s) 1602, one or more memory device(s) 1604, one or more interface(s) 1606, one or more mass storage device(s) 1608, and one or more Input/Output (I/O) device(s) 1610, all of which are coupled to a bus 1612. Processor(s) 1602 include one or more processors or controllers that execute instructions stored in memory device(s) 1604 and/or mass storage device(s) 1608. Processor(s) 1602 may also include various types of computer-readable media, such as cache memory.

Memory device(s) 1604 include various computer-readable media, such as volatile memory (e.g., random access memory (RAM)) and/or nonvolatile memory (e.g., read-only memory (ROM)). Memory device(s) 1604 may also include rewritable ROM, such as Flash memory.

Mass storage device(s) 1608 include various computer readable media, such as magnetic tapes, magnetic disks, optical disks, solid state memory (e.g., Flash memory), and so forth. Various drives may also be included in mass storage device(s) 1608 to enable reading from and/or writing to the various computer readable media. Mass storage device(s) 1608 include removable media and/or non-removable media.

I/O device(s) 1610 include various devices that allow data and/or other information to be input to or retrieved from computing device 1600. Example I/O device(s) 1610 include cursor control devices, keyboards, keypads, microphones, monitors or other display devices, speakers, printers, network interface cards, modems, lenses, CCDs or other image capture devices, and the like.

Display device(s) 1605 includes any type of device capable of displaying information to one or more users of computing device 1600. Examples of display device 1605 include a monitor, display terminal, video projection device, and the like.

Interface(s) 1606 include various interfaces that allow computing device 1600 to interact with other systems, devices, or computing environments. Example interface(s) 1606 include any number of different network interfaces, such as interfaces to local area networks (LANs), wide area networks (WANs), wireless networks, and the Internet. Other interface(s) may include user interface 1607 and peripheral device interface 1609. The interface(s) 1606 may also include one or more user interface elements. The interface(s) 1606 may also include one or more peripheral interfaces such as interfaces for printers, pointing devices (mice, track pad, or any suitable user interface now known to those of ordinary skill in the field, or later discovered), keyboards, and the like.

Bus 1612 allows processor(s) 1602, memory device(s) 1604, display device(s) 1605, interface(s) 1606, mass storage device(s) 1608, and I/O device(s) 1610 to communicate with one another, as well as other devices or components coupled to bus 1612. Bus 1612 represents one or more of several types of bus structures, such as a system bus, PCI bus, IEEE 1394 bus, USB bus, and so forth.

For purposes of illustration, programs and other executable program components are shown herein as discrete blocks, although it is understood that such programs and components may reside at various times in different storage components of computing device 1600, and are executed by processor(s) 1602. Alternatively, the systems and procedures described herein can be implemented in hardware, or a combination of hardware, software, and/or firmware. For example, one or more application specific integrated circuits (ASICs) can be programmed to carry out one or more of the systems and procedures described herein. As used herein, the term "module" is intended convey the implementation apparatus for accomplishing a process, such as by hardware, or a combination of hardware, software, and/or firmware, for the purposes of performing all or parts of query operations.

Figure 17:
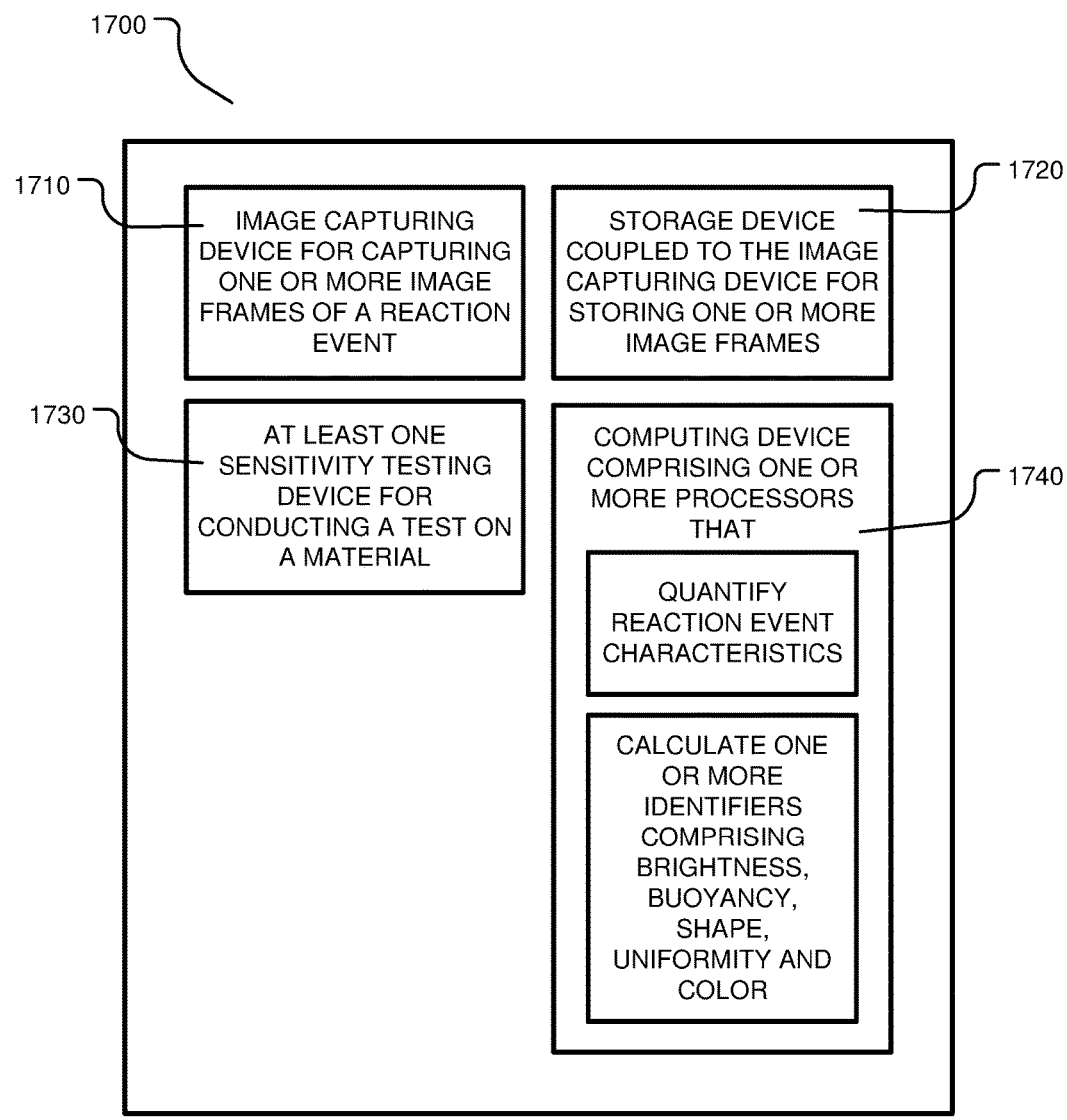
FIG. 17 is an implementation of a system for evaluating a reaction event of a material in accordance with the teachings and principles of the disclosure.

Referring now to FIG. 17, there is illustrated an implementation of a system for evaluating a reaction event of a material in accordance with the teachings and principles of the disclosure. The system 1700 for evaluating a reaction event of a material may comprise an image capturing device 1710 that captures one or more image frames of the reaction event. The system 1700 may also comprise a storage device 1720 coupled to the imaging capturing device 1710 for storing the one or more image frames in memory. The system 1700 may further comprise at least one sensitivity testing device 1730 for conducting a test on the material. The system 1700 may further comprise a computing device 1740 comprising one or more processors, wherein the storage device stores instructions that, when executed by one or more processors, cause the processors to: quantify one or more reaction event characteristics, wherein the instructions further cause the one or more processors to calculate one or more identifiers comprising brightness, buoyancy, shape, and uniformity of the reaction event. In an implementation, the system 1700 may comprise a computing device 1740 comprising one or more processors, wherein the storage device stores instructions that, when executed by one or more processors, cause the processors to: quantify one or more reaction event characteristics, wherein the instructions further cause the one or more processors to calculate one or more identifiers comprising brightness, buoyancy, shape, uniformity and color of the reaction event.

In an implementation of the disclosure, computer program products may comprise computer readable storage media that stores instructions for evaluating a reaction event of a material that, when executed by one or more processors, cause the one or more processors to: capture one or more image frames of a baseline reaction event using an image capturing device, wherein a baseline data set is obtained from the baseline reaction event and wherein the baseline data set does not comprise all information of the material; store the one or more image frames of the baseline reaction event in computer readable memory; capture one or more image frames of a trial reaction event using an image capturing device, wherein a trial data set is obtained from the trial reaction event and wherein the trial data set comprises information relating to the material; store the one or more image frames of the trial reaction event in computer readable memory; quantify the baseline data set and the trial data set, wherein the quantifying process further comprises one or more of the following identifiers: calculate brightness from the one or more image frames of the baseline reaction event and the trial reaction event; calculate the buoyancy from the plurality of image frames of the baseline reaction event and the trial reaction event; calculate the shape from the one or more image frames of the baseline reaction event and the trial reaction event; and calculate the uniformity from the one or more image frames of the baseline reaction event and the trial reaction event; compare the quantified trial data set to the quantified baseline data set; and determine whether a reaction event occurred based on the comparison of the quantified trial data set to the quantified baseline data set.

In another implementation of the disclosure, computer program products may comprise computer readable storage media that stores instructions for evaluating a reaction event of a material that, when executed by one or more processors, cause the one or more processors to: capture one or more image frames of a baseline reaction event using an image capturing device, wherein a baseline data set is obtained from the baseline reaction event and wherein the baseline data set does not comprise all information of the material; store the one or more image frames of the baseline reaction event in computer readable memory; capture one or more image frames of a trial reaction event using an image capturing device, wherein a trial data set is obtained from the trial reaction event and wherein the trial data set comprises information relating to the material; store the one or more image frames of the trial reaction event in computer readable memory; quantify the baseline data set and the trial data set, wherein the quantifying process further comprises one or more of the following identifiers: calculate brightness from the one or more image frames of the baseline reaction event and the trial reaction event; calculate the buoyancy from the plurality of image frames of the baseline reaction event and the trial reaction event; calculate the shape from the one or more image frames of the baseline reaction event and the trial reaction event; calculate the uniformity from the one or more image frames of the baseline reaction event and the trial reaction event; and calculate the color from the one or more image frames of the baseline reaction event and the trial reaction event; compare the quantified trial data set to the quantified baseline data set; and determine whether a reaction event occurred based on the comparison of the quantified trial data set to the quantified baseline data set.

In accordance with the features and combinations described above, the method for evaluating a reaction event of an energetic material may comprise: capturing a single or plurality of image frames of a baseline reaction event using an image capturing device, wherein a baseline data set is obtained from the baseline reaction event and wherein the baseline data set does not comprise all information of the energetic or reactive material; storing the image frame or frames of the baseline reaction event in computer readable memory; capturing a single or plurality of image frames of a trial reaction event using an image capturing device, wherein a trial data set is obtained from the trial reaction event and wherein the trial data set comprises information relating to the energetic material; storing the plurality of image frames of the trial reaction event in computer readable memory; quantifying the baseline data set and the trial data set, wherein the quantifying process further comprises one or more of the following identifiers: calculating brightness from the single or plurality of image frames of the baseline reaction event and the trial reaction event; calculating the buoyancy from the plurality of image frames of the baseline reaction event and the trial reaction event; calculating the shape from the single or plurality of image frames of the baseline reaction event and the trial reaction event; calculating the uniformity from the single or plurality of image frames of the baseline reaction event and the trial reaction event; and calculating the color from the single or plurality of image frames of the baseline reaction event and the trial reaction event; comparing the quantified trial data set to the quantified baseline data set; and determining whether a reaction event occurred based on the comparison of the quantified trial data set to the quantified baseline data set.

It will be appreciated by those familiar with sensitivity testing of energetic materials that the disclosure improves upon known techniques used in the industry by, inter alia, using five unique identifiers or quantifiers relating to the images identified as being of interest and significant. Those identifiers or quantifiers include: brightness, shape, buoyancy, uniformity or the color of the reaction event. The disclosure also detects decomposition or reaction of energetic materials using the above disclosed systems and methods. The system and processes disclosed may also be advantageous in that multiple characteristics of the images are simultaneously quantified to determine if a reaction has occurred.

In the foregoing Detailed Description, various features of the disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the appended claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure. Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system for evaluating a reaction event of a material comprising:
    an image capturing device that captures one or more image frames of the reaction event;
    a storage device coupled to the imaging capturing device for storing the one or more image frames in memory;
    at least one sensitivity testing device for conducting a test on the material; and
    a computing device comprising one or more processors;
    wherein the storage device stores instructions that, when executed by one or more processors, cause the processors to,
        quantify one or more reaction event characteristics based on the image frames, wherein quantifying the one or more reaction event characteristics comprises calculating one or more identifiers comprising brightness, buoyancy, shape, or uniformity of the reaction event; and
    wherein the instructions further cause the one or more processors to determine and store a characterization of the reaction event as a go or no-go reaction based the one or more reaction event characteristics;
    wherein calculating the one or more identifiers further comprises calculating color; wherein the image capture device is configured to capture the one or more image frames are captured based on a triggering event that begins a capture session and an expected length of a baseline reaction event or the reaction event that ends the capture session, wherein the one or more frames are recorded and identified as one or more frames of interest;
    wherein the instructions further cause the one or more processors to identify one or more significant frames from among the frames of interest, wherein the instructions cause the one or more processors to identify the one or more significant frames by analyzing each of the frames of interest for a change in an image property and identifying a frame as a significant frame when there is a change in the image property;
    wherein the instructions further cause the one or more processors to convert a color image for each of the significant frames to a grayscale image; and
    wherein the instructions further cause the one or more processors to filter the grayscale image by giving each pixel a grayscale brightness value, wherein instructions cause the one or more processors to attenuate the grayscale brightness value as a distance from a center of a brightest point increases.

2. The system of claim 1, wherein the triggering event comprises an image based trigger, sound based trigger, current based trigger, proximity based trigger, or interrupt based trigger.

3. The system of claim 1, wherein the one or more frames of interest are analyzed for an indication of a significant difference from a previous frame of interest and are then identified as one or more significant frames.

4. The system of claim 3, wherein the instructions further cause the one or more processors to apply a background map to each of the significant frames that are identified, wherein the background map eliminates ambient information from the quantization of the significant frames.

5. The system of claim 4, wherein the instructions cause the one or more processors to create the background map by standardizing all pixels in each of the significant frames to a baseline brightness value to thereby eliminate all visual effects of the ambient surroundings, such that the analysis is focused directly on an analysis site.

6. The system of claim 1, wherein the image property of one or more of the frames of interest comprises an average brightness and wherein the instructions cause the one or more processors to identify one or more of the frames of interest as the significant frame when its brightness is more than 1-10 standard deviations greater than a mean brightness of the one or more frames of interest.

7. The system of claim 1, wherein instructions cause the one or more processors to attenuate using a non-linear attenuation following a hyperbolic tangent distribution.

8. The system of claim 1, wherein the instructions cause the processors to calculate a brightness by assigning a brightness value to each pixel, and a brightness value for a given frame that comprises a sum of all pixel values or multiple of all pixel values in the given frame, wherein the pixel values comprise one or more of red pixel values, blue pixel values, or green pixel values.

9. The system of claim 1, wherein the instructions cause the processors to calculate a buoyancy based on a difference between an average center of mass, based on a grayscale or color pixel value, and a value of a center of mass for a plurality of image frames.

10. The system of claim 1, wherein the instructions cause the one or more processors to calculate the uniformity based on a reshaped pixel matrix where a number of peaks in the reshaped pixel matrix is determined, summed and normalized.

11. The system of claim 1, wherein the instructions cause the one or more processors to calculate shape by determining an effective aspect ratio of a frame by performing matrix multiplication with the pixel matrix and a weighting matrix minus the product of the brightness and center of mass in the horizontal and vertical directions, and normalizing the resulting value and summing those resulting values over all frames of interest.

12. The system of claim 1, wherein the color of each frame is quantified by the sum of the product of the red, green, blue, or combination thereof of pixel values and a weighting factor.

13. The system of claim 1, wherein the storage device stores a mean baseline value and a baseline standard deviation for one or more of the identifiers of brightness, buoyancy, shape, uniformity, or color for the baseline reaction event.

14. The system of claim 13, wherein the instructions further cause the one or more processors to normalize the identifiers of brightness, buoyancy, shape, uniformity, or color for the reaction event and assigns a value to each identifier, wherein normalization is based on the mean baseline value and the standard deviation for brightness, buoyancy, shape, uniformity, or color of the baseline reaction event.

15. The system of claim 14, wherein the instructions cause the processors to: subtract the mean baseline value of the baseline identifiers of brightness, buoyancy, shape, uniformity, or color from the values of each respective trial identifiers of brightness, buoyancy, shape, uniformity, or color; and divide by the baseline standard deviation for the respective identifier.

16. The system of claim 15, wherein the instructions further cause the processors to combine the normalized value of each identifier to yield a single identifying value that reflects a difference between the trial reaction event and the baseline reaction event.

17. The system of claim 16, wherein the instructions cause the one or more processors to determine the identifying value from the summation of the trial identifiers of brightness, buoyancy, shape, uniformity, or color and wherein the identifying value is proportional to the number of standard deviations from the baseline values.

18. The system of claim 16, wherein the instructions further cause the one or more processors to determine a threshold value for characterizing the reaction event as a go or no-go reaction, such that if the identifying value of the trial identifiers of the reaction event is greater than the threshold, the trial is then designated as a go reaction; and if the identifying value of the trial identifiers of the reaction event is less than the threshold, the trial is then designated as a no-go reaction.

19. The system of claim 3, wherein the instructions further cause the one or more processors to calculate a Type I (false positive) error and Type II (false negative) error by identifying the number of falsely identified Go's and No-Go's based on the quantified reaction characteristics of brightness, buoyancy, shape, uniformity, or color.

20. The system of claim 19, wherein the instructions cause the one or more processors to calculate the Type I error and Type II error in a recursive manner, wherein a distribution of the identifying value of the trial identifiers for the go reactions and a distribution of the identifying value of the trial identifiers for the no-go reactions are located in a continuous probability distribution.

21. The system of claim 20, wherein the instructions cause the one or more processors to optimize a value of the Type I error or the Type II error by changing the method or methods to distinguish a reaction from a non-reaction to reflect the appropriate amount of risk obtained in sensitivity test results.

22. The system of claim 21, wherein the instructions further cause the one or more processors to:
  reclassify a portion of the reactions identified as go reactions based on the estimated probabilities of go reactions and no-go reactions at a given identifying value or collection of identifying values, and reclassify a portion of the reactions identified as no-go reactions based on the estimated probabilities of go reactions and no-go reactions at a given identifying value or collection of identifying values;
  update the values for go reactions and no-go reactions; and
  re-estimate the distribution of go reactions and no-go reactions based on the updated values for go reactions and no-go reactions at each identifying value or collection of identifying values;
  wherein the proportion of go reactions and no-go reactions at each identifying value or collection of identifying values are re-estimated based on the updated distribution of go reactions and no-go reactions;
  wherein the instructions cause the processors to repeatedly reclassify, update, and re-estimate until convergence.

23. The system of claim 22, wherein the proportion of go reactions to no-go reactions at a given identifying value or collection of identifying values is estimated from a ratio of the probability of a go reaction to a no-go reaction at a given identifying value or collection of identifying values, wherein the probability of a go reaction is found from the estimated distribution of go reactions and the probability of a no-go reaction is found from the estimated distribution of no-go reactions.

24. The system of claim 19, wherein the Type I error is minimized to reduce the risk to personnel during operations, storage, and transportation.

25. Non-transitory computer readable storage media storing instructions for evaluating a reaction event of a material that, when executed by one or more processors, cause the one or more processors to:
capture one or more image frames of a baseline reaction event using an image capturing device, wherein a baseline data set is obtained from the baseline reaction event and wherein the baseline data set does not comprise all information of the material;
store the one or more image frames of the baseline reaction event in computer readable memory;
capture one or more image frames of a trial reaction event using an image capturing device, wherein a trial data set is obtained from the trial reaction event and wherein the trial data set comprises information relating to the material;
store the one or more image frames of the trial reaction event in computer readable memory;
quantify the baseline data set and the trial data set, wherein the quantifying process further comprises calculating one or more of the following identifiers:
brightness from the one or more image frames of the baseline reaction event and the trial reaction event;
buoyancy from the plurality of image frames of the baseline reaction event and the trial reaction event;
shape from the one or more image frames of the baseline reaction event and the trial reaction event; and
uniformity from the one or more image frames of the baseline reaction event and the trial reaction event;
compare the quantified trial data set to the quantified baseline data set; and
determine whether a reaction event occurred based on the comparison of the quantified trial data set to the quantified baseline data set
wherein calculating the one or more identifiers comprises color from the one or more image frames of the baseline reaction event and the trial reaction event; wherein the one or more image frames are captured based on a triggering event that begins a capture session and an expected length of the baseline reaction event and the trial reaction event that ends the capture session, wherein the frame or frames are recorded and identified as frame(s) of interest;
wherein the instructions further cause the one or more processors to identify significant frames from among the frames of interest, wherein each of the frames of interest are analyzed for a change in an image property and a frame is identified as a significant frame when there is a change in the image property;
wherein the instructions further cause the one or more processors to convert a color image for each of the significant frames identified to a grayscale image, and filter each of the grayscale images; and
wherein the instructions further cause the one or more processors to weight the filter by giving each pixel a grayscale brightness value, wherein the filter is centered on the brightest part of the grayscale image and then the grayscale brightness value is attenuated as a distance from a center of a brightest point increases.

26. The readable storage media of claim 25, wherein the triggering event is an image based trigger, or a sound based trigger, or a current based trigger.

27. The readable storage media of claim 25, wherein the frame or frames of interest are analyzed for an indication of a change obtained during the baseline reaction event and the trial reaction event, wherein the frame or frames of interest that indicate a change are separated from the frame or frames of interest where there is no indication of a change and the separated frames are identified as significant frame or frames.

28. The readable storage media of claim 27, wherein the instructions further cause the one or more processors to create a background map for each of the significant frames.

29. The readable storage media of claim 28, wherein the background map is created by standardizing all pixels in each of the significant frames to a baseline brightness value to thereby eliminate all visual effects of the ambient surroundings, such that the analysis is focused directly on an analysis site.

30. The readable storage media of claim 25, wherein each of the frames of interest are analyzed and compared to an average brightness and a frame is identified as a significant frame when its brightness is more than 5 standard deviations greater than a mean brightness.

31. The readable storage media of claim 25, wherein the attenuation is non-linear and follows a hyperbolic tangent distribution.

32. The readable storage media of claim 25, wherein the instructions further cause the one or more processors to assign a brightness value to each pixel in each of the significant frames, wherein the brightness value for a given significant frame is the sum of all pixel values in that significant frame normalized by resolution and the number of significant frames identified in the baseline reaction event or the trial reaction event.

33. The readable storage media of claim 32, wherein the instructions further cause the one or more processors to assign a buoyancy value, wherein buoyancy is calculated from the difference between an average center of mass, based on a grayscale pixel value, and the value of the center of mass for the first of the one or more image frames.

34. The readable storage media of claim 33, wherein uniformity is found from a reshaped pixel matrix where the number of peaks in the reshaped pixel matrix is found, summed and then normalized.

35. The readable storage media of claim 34, wherein the instructions further cause the one or more processors to identify the shape of each of the significant frames, wherein shape is calculated by weighting each significant frame's shape by performing matrix multiplication with the pixel matrix and the weighting matrix minus the product of the brightness and center of mass in the horizontal and vertical directions, and normalize the resulting value and summing those resulting values over all significant frames.

36. The readable storage media of claim 33, wherein color is quantified by the sum of the product of the red, green, blue, or combination thereof of pixel values and a weighting factor.

37. The readable storage media of claim 25, wherein the instructions further cause the one or more processors to calculate a mean baseline value and a baseline standard deviation for each of the identifiers of brightness, buoyancy, shape, uniformity, or color for the baseline reaction event and storing the results in computer readable memory.

38. The readable storage media of claim 36, wherein the instructions further cause the one or more processors to normalize the identifiers of brightness, buoyancy, shape, uniformity, or color for the trial reaction event and assigning a value to each identifier, wherein normalizing is based on the mean baseline value and the standard deviation for brightness, buoyancy, shape and uniformity of the baseline reaction event.

39. The readable storage media of claim 37, wherein normalizing each of the identifiers of brightness, buoyancy, shape, uniformity, or color for the trial reaction event further comprises subtracting the mean baseline values of the baseline identifiers of brightness, buoyancy, shape, uniformity, or color from the values of each of the trial identifiers of brightness, buoyancy, shape, uniformity or color, and then dividing the result by the baseline standard deviation for that identifier.

40. The readable storage media of claim 38, wherein the normalized value of each identifier is combined to yield a single identifying value that reflects a difference between the trial reaction event and the baseline reaction event.

41. The readable storage media of claim 39, wherein the identifying value is determined from the summation of the trial identifiers of brightness, buoyancy, shape, uniformity, or color and the identifying value is proportional to the number of standard deviations from the baseline values.

42. The readable storage media of claim 40, wherein the instructions further cause the one or more processors to set a specified threshold value to determine whether a reaction event falls within predetermined parameters characterizing the reaction event as a go or no-go reaction, such that if the identifying value of the trial identifiers of the reaction event is greater than the specified threshold, the trial is then designated as a go reaction; and if the identifying value of the trial identifiers of the reaction event is less than the specified threshold, the trial is then designated as a no-go reaction.

43. The readable storage media of claim 41, wherein the instructions further cause the one or more processors to calculate Type I error and Type II error for the specified threshold.

44. The readable storage media of claim 42, wherein a recursive method is used to calculate the Type I error and Type II error, wherein the distribution of the identifying value of the trial identifiers for the go reactions and the distribution of the identifying value of the trial identifiers for the no-go reactions are located in a continuous probability distribution.

45. The readable storage media of claim 43, wherein the value of the Type I error or the Type II error is optimized by changing the threshold value to reflect the appropriate amount of risk obtained by the sensitivity test results.

46. The readable storage media of claim 44, wherein the instructions further cause the one or more processors to:

reclassify a portion of the reactions identified as go reactions to no-go reactions based on the estimated probabilities of go reactions and no-go reactions at a given identifying value or collection of identifying values, and reclassifying a portion of the reactions identified as no-go reactions to go reactions based on the estimated probabilities of go reactions and no-go reactions at a given identifying value or collection of identifying values;

update the values for go reactions and no-go reactions;

re-estimate the distribution of go reactions and no-go reactions based on the updated values for go reactions and no-go reactions at each identifying value or collection of identifying values;

re-estimate the proportion of go reactions and no-go reactions at each identifying value or collection of identifying values based on the updated distribution of go reactions and no-go reactions;

wherein this process is recursively completed to convergence.

47. The readable storage media of claim 45, wherein the instructions further cause the one or more processors to:

estimate the proportion of go reactions to no-go reactions at a given identifying value or collection of identifying values from a ratio of the probability of a go reaction to a no-go reaction at a given identifying value or collection of identifying values, wherein the probability of a go reaction is found from the estimated distribution of go reactions and the probability of a no-go reaction is found from the estimated distribution of no-go reactions.

48. The readable storage media of claim 42, wherein the instructions further cause the one or more processors to adjust the threshold to optimize the Type I error and the Type II error to minimize the risk to personnel during operations, storage, and transportation.

* * * * *